United States Patent [19]

Card et al.

[11] Patent Number: 4,654,440

[45] Date of Patent: Mar. 31, 1987

[54] CATALYSTS FOR SELECTIVE PREPARATION OF AMINES OR NITRILES FROM ALKANOLS

[75] Inventors: Roger J. Card, Stamford; Joseph L. Schmitt, Jr., Bethel, both of Conn.

[73] Assignee: American Cyanamid Company, Stamford, Conn.

[21] Appl. No.: 173,781

[22] Filed: Jul. 30, 1980

[51] Int. Cl.$^4$ .............................................. C07C 85/06
[52] U.S. Cl. ..................................... 564/479; 564/402
[58] Field of Search ............................... 564/479, 402

[56] References Cited

U.S. PATENT DOCUMENTS

| | | | |
|---|---|---|---|
| 2,349,461 | 5/1944 | Pratt et al. | 564/479 X |
| 2,389,500 | 11/1945 | Goshorn | 260/585 |
| 3,475,344 | 10/1969 | Adam et al. | 564/479 X |
| 4,206,149 | 6/1980 | Slaugh | 564/479 |

FOREIGN PATENT DOCUMENTS 2749066  5/1978  Fed. Rep. of Germany ...... 564/479

45-38803  8/1970  Japan ................................. 564/479

OTHER PUBLICATIONS

Kirk–Othmer, *Encyclopedia of Chemical Technology* (New York, John Wiley & Sons), vol. 2, pp. 276–277.

*Primary Examiner*—Charles F. Warren
*Attorney, Agent, or Firm*—Gordon L. Hart

[57] ABSTRACT

Alkanols, e.g., octanol, are reacted in gas mixtures with excess ammonia and preferably hydrogen at temperatures from 180° to 340° C. over supported catalytic oxides of copper, manganese, antimony and tin at atmospheric to moderate pressures. Depending on the selected catalyst and selected temperature, yields of 40% to 98% of monoalkyl amines or nitriles are produced. Other organic substrates, such as aromatic alcohols and aldehydes, aliphatic aldehydes, esters and primary and secondary amines can also be converted to nitriles at yields greater than 90%. The process is readily adaptable for continuous flow processing.

4 Claims, No Drawings

CATALYSTS FOR SELECTIVE PREPARATION OF AMINES OR NITRILES FROM ALKANOLS

The invention relates to catalytic reaction of mixtures of ammonia, hydrogen and a selected alkanol to produce the corresponding alkyl amine or nitrile or both. More particularly, the invention is directed to the reactions of alkanols having 2 to 20 carbon atoms in gas-phase mixtures with ammonia and hydrogen in contact with solid supported metal oxide catalysts at elevated reaction temperatures and at atmospheric to moderate pressures to produce monoalkyl amines or nitriles or both.

An object of the invention is to provide preferred catalysts for gas-phase catalytic reactions of alkanols with ammonia and hydrogen to achieve relatively high selectivity of conversion to the monoalkyl amine. In another aspect of the invention, the reaction conditions may be adjusted and the catalyst selected to achieve relatively high selectivity of conversion of the alkanols to corresponding nitriles. Other organic substrates such as aldehydes, esters and primary and secondary amines can also be converted to the corresponding nitriles at relatively high selectivity of conversion.

Catalytic snythesis of amines and nitriles by ammonolysis of alcohols has been described. Various prior art processes include, typically, amination reactions at elevated temperatures and high pressures in the presence of metal catalysts. The present invention is particularly adaptable for continuous processing because the reactions can be carried out at suitably short contact times, by contacting a mixture of all the reactants in gas-phase with solid heterogeneous catalysts and without the need for high pressure. Yields usually above 40 percent of the desired amine or nitrile product can be achieved by a single pass of the gas-phase reaction mixture through a heated bed of the solid catalyst at atmospheric pressure.

The catalysts that are active and are suitably selective for making amines in accordance with the invention are oxides of copper, manganese, antimony and tin on alumina supports. The catalytic metal oxides may be used singly or in a combination of several of the selected oxides on the support, as will be explained in more detail. Copper oxide is the most active of the selected catalysts and may be used for high selectivity of conversion to either amines or nitriles, by selecting a suitable reaction temperature that will favor selectivity of conversion to the product wanted. For making nitriles, copper oxide may be used alone or in combination with zinc oxide on alumina support. Other catalysts found effective for high yields of nitriles include mixed oxides of copper and nickel on alumina and oxide of nickel on a high-surface-area carbon support.

The reaction temperatures for production of amines according to the invention will be in the range from about 180° to about 340° C. When using any of the catalysts, the degree of total conversion of the alcohol will tend to increase as the reaction temperature increases in the defined range. Selectivities of conversion to amines or nitriles will vary as the reaction temperature is varied, and the optimum temperature for amine or nitrile selectivity will differ with the different catalysts. When using copper oxide on alumina, the percent conversion of alcohol will increase as reaction temperature is increased within the defined range, generally from less than 50% at 180° C. to nearly 100% conversion at temperatures above 250° C. With the most preferred copper catalysts, the selectivity of conversion to amine will be highest at the lowest temperatures in the defined range, decreasing quickly to near zero amine selectivity at a temperature of about 260° C. or higher. Conversely, as the temperature is increased while using the copper catalysts, the selectivity of conversion of alcohol to its corresponding nitrile increases from less than 50% selectivity at 180° C. to the maximum selectivity, in some cases over 90% nitrile selectivity, at about 260° C. and higher. Contact times of 0.1 to 10 seconds may be used, with about 1 to 3 seconds preferred. Pressures may be 1 to 30 atm. or higher, with pressures of 1–10 atm. particularly preferred.

The catalysts in which antimony, tin or manganese is the active metal will differ from the copper catalysts most significantly by the fact that the selectivity of conversion of alcohol to nitrile remains at zero, or at very low values, at all temperatures in the range from 180° C. to 340° C. The percent conversion of the alcohol reactant increases from values below 50% at 180°–200° C. to conversion near 100% at 340° C. The selectivity of conversion of alcohol to the monoamine will usually increase with increase of reaction temperature when using the antimony and tin catalysts; with the manganese catalysts the selectivity of conversion to monoamine tends to remain about constant with increase of temperature.

The reactant gas feed mixtures preferred for use in the invention are mixtures comprising 5 to 20 moles ammonia per one mole of the alkanol reactant. The mixtures will preferably also contain hydrogen and we prefer a mixture in which the mole ratio of ammonia to hydrogen is in the range from about 4 to 1 to about 1 to 4. A particularly preferred mixture is $NH_3:H_2:ROH=20:5:1$ (molar). This is the mixture that was used for all of the experiments described in the tables herein.

The effect of variations of contact time on the process results have not been studied as extensively as other factors, but at various lengths of contact time in the range from about ½ second to about 5 seconds, the differences observed in percent conversion and selectivity at several different contact times were only different in degree as would be expected.

The effect of the concentration of catalyst metal on the catalyst supports was observed using some of the catalytically active metals mentioned above in varied concentrations. In general, increasing the metal concentration on the support would give a catalyst with increased activity, but the selectivity characteristics of the catalyst were not altered.

The selection of alumina as the catalyst support appears to be an important contributor to the activity and selectivity characteristics of the catalysts used in most embodiments of this invention. Gamma alumina supports having surface area in the range about 100–350 $m^2/gm$ is presently the most preferred support and one having surface area about 300 $m^2/gm$ is used in the following examples which describe in more detail several preferred embodiments of the invention. In these examples n-octanol is selected as a typical alkanol for demonstration of the invention by detailed examples. Other alumina supports and other alkanols within the ranges defined above may be used instead of those selected for the examples herein.

EXAMPLE 1

In order to investigate the activity of different metals for the conversion of 1-octanol to n-octylamine, catalysts were prepared by impregnating Y-$Al_2O_3$ extrudates having surface area=300 $m^2$/g and pore volume 0.7 cc/g with aqueous solutions of various soluble metal salts. Generally soluble nitrates or chlorides of the selected metals were used and the amount of solution was adjusted so that the pore volume of the $Al_2O_3$ was just saturated. The impregnated support particles were dried in an air oven and calcined in flowing air for 2 hours at 500° C. The metal salts are converted to the oxides by the calcining.

The catalysts thus prepared were packed into a tubular, continuous flow reactor and a gas mixture of $NH_3$, $H_2$ and 1-octanol vapor was passed through the reactor at a molar ratio of 20:5:1 respectively. For each catalyst the reaction was operated at several different temperatures in the range from 180° to 340° C. The product gas mixture taken from the reactor at each selected operating temperature was condensed and the liquids were collected in methanol and analyzed by gas chromatography. A summary of the significant results is tabulated in Table I.

The results illustrate that wereas Cu can give high selectivities to either n-octylamine or octanenitrile, depending on the selected reaction temperature used, Mn, Sb and Sn are all capable of giving 25% and higher percent selectivities to n-octylamine at relatively high reaction temperatures without forming large amounts of octanonitrile.

EXAMPLE 2

In order to investigate the effect of metal concentration on catalytic behavior, catalysts were prepared as described in Example 1 above but having several different concentrations of the same active metal on the supports. By submitting these catalysts to the testing procedure described in Example 1, the results shown in Table II were obtained. The test results show that increasing the concentration of active metal in the reactor increases the activity of the catalyst as would have been expected. Except at very low metal loadings the selectivity characteristics did not vary significantly at different metal loadings.

EXAMPLE 3

Catalysts containing 5 wt. % Cu were prepared as described in Example 3 except using three different solid supports. After putting these catalysts through the standard test procedure, the results shown in Table III were obtained. These results show that the $Al_2O_3$ is the preferred support for the copper catalysts.

EXAMPLE 4

A catalyst comprising 5% antimony on alumina, prepared as described in Example 1 was tested at three different experimental conditions. In each case the reactants molar ratio was held constant, but the total feed rate and/or the catalyst bed volume were varied so that different contact times were obtained. Results are shown in Table IV.

These results demonstrate that although overall 1-octanol conversion can be increased by increasing contact time, the selectivity to n-octylamine is not significantly affected by the changes in contact time.

EXAMPLE 5

A series of catalysts containing two different catalytic metals were prepared on the $Al_2O_3$ support by the method described in Example 1, and tested under standard test conditions. Results are shown in Table V.

These results show that by varying the relative amounts of Cu and Mn the selectivity of the catalyst toward either n-octylamine or octanenitrile can be significantly altered. For example, high selectivity to n-octylamine can be obtained with relatively little octanenitrile being produced. The activities and selectivities of Cu-Mn and Cu-Sb catalysts are similar. If high selectivity to octanenitrile is desired, Cu-Zn catalysts can be used effectively.

EXAMPLE 6

For conversion of alcohols to nitriles some of the catalysts which were found to produce very high yields of nitrile are described in Table VI. These catalysts were prepared and tested by the methods described in Example 1 except when a carbon support was used, the calcination temperature was reduced to 300° C. Catalysts made with antimony, tin and manganese did not produce significant nitrile yields in the process described. Vanadium, rhodium, and platinum catalysts produced substantial yields that were below 40%.

EXAMPLE 7

Using catalysts of 15% by wt Cu on alumina prepared as described in Example 1, nitriles in high yields were obtained using a variety of substrates other than octanenitrile in the feed composition for a process carried out as described in Example 1. The substrates used and the results are tabulated in Table VII.

TABLE I

ACTIVITIES OF DIFFERENT METALS

| Catalyst Composition Percent Catalytic Metal by Wt. on Alumina Support | Temperature at Which Conversion of Octanol Reaches 100% | Temperature and Percent Selectivity to n-octylamine at 50% Conversion | | Maximum Percent Selectivity to Octanenitrile in the Temperature Range 200–340° C. |
|---|---|---|---|---|
| | | Temp. | Amine Selectivity | |
| 15% Cu | 240° C. | 201° | 53% | 97% at 280° |
| 5% Mn | 340 | 270° | 50% | <5% |
| 5% Sn | 310 | 240° | 25% | <5% |
| 5% Sb | 340 | 260° | 40% | <5% |
| 5% V | 280 | 250° | 20% | 20% at 340° |
| 2% Pt | 310 | 250° | <5% | 40% at 280–310° |
| 2% Rh | 310 | 255° | 10% | 50% at 220° |

TABLE II

EFFECT OF METAL LOADING

| Metal | Wt. % Elements Metal in the Catalyst | Octanol Percent Conversion at 280° C. |
|---|---|---|
| Cu | 5 | 45% |

TABLE II-continued
EFFECT OF METAL LOADING

| Metal | Wt. % Elements Metal in the Catalyst | Octanol Percent Conversion at 280° C. |
|---|---|---|
| Cu | 15 | 100 |
| Cu | 30 | 100 |
| Sb | 5 | 70 |
| Sb | 15 | 85 |

TABLE III
EFFECT OF CATALYST SUPPORT

| Catalyst Composition | Support | Support S.A. | Octanol Conversion at 280° C. |
|---|---|---|---|
| 5% Cu | Al₂O₃ | 300 m2/g | 45% |
| 5% Cu | 80% Al₂O₃ + 18% SiO₂ | 30 | 10 |
| 5% Cu | Carbon | 550 | <5 |

TABLE IV
EFFECT OF CONTACT TIME

| Catalyst Composition | Contact Time | Percent Octanol Conversion at 260° C. | Percent Selectivity to n-octylamine at 50% Octanol Conversion |
|---|---|---|---|
| 5% Sb | 0.5 sec. | 25% | 50% at 300° C. |
| 5% Sb | 2.0 sec. | 50 | 45% at 260° C. |
| 5% Sb | 4.0 sec. | 80 | 50% at 230° C. |

TABLE V
ACTIVITY OF BIMETALLIC CATALYSTS

| Catalyst Composition | Maximum Percent Selectivity to n-octylamine | Maximum Percent Selectivity to Octanenitrile in Temp. Range 245–320° |
|---|---|---|
| 5% Cu | 62% at 247° | 88% at 305° |
| 5% Mn | 65% at 305–320° | 0 |
| 4.3% Cu + 1.0% Mn | 81% at 273° | 69% at 318° |
| 3.3% Cu + 2.0% Mn | 80% at 303° | 46% at 320° |
| 2.2% Cu + 2.9% Mn | 73% at 275° | 8% at 320° |
| 2.6% Cu + 5.0% Sb | 80% at 225° | 5% at 320° |
| 4.9% Cu + 5.0% Zn | 30% at 223° | 97% at 300° |

TABLE VI
HIGH NITRILE YIELDS

| Catalyst | Contact time (sec) | Temperature (°C.) | Octanenitrile Yield (%) |
|---|---|---|---|
| 30% Cu on Alumina | 0.5 | 300 | 98 |
| 4.9% Cu + 5.0% Zn on Alumina | 2.0 | 300 | 97 |
| 5% Cu + 5% Ni on Alumina | 0.5 | 300 | 84 |
| 5% Ni on carbon | 2.0 | 338 | 77 |

TABLE VII
OTHER SUBSTRATES

| Starting Material | Product | Temperature (°C.) | Yield (%) |
|---|---|---|---|
| benzaldehyde | benzonitrile | 300 | 95 |
| benzyl alcohol | benzonitrile | 300 | 96 |
| benzylamine | benzonitrile | 300 | 95 |
| p-methoxybenz-aldehyde | p-methoxybenzo nitrile | 280 | 95 |
| ethanol | acetonitrile | 325 | 87 |
| ethyl acetate | acetonitrile | 325 | 95 |
| n-butanol | butyronitrile | 325 | 96 |
| n-octylamine | n-octanenitrile | 325 | 92 |
| di-(n-octyl)amine | n-octanenitrile | 325 | 95 |

We claim:

1. A process for synthesis of an amine from an alkanol which comprises contacting a gas-phase reaction mixture of alkanol, ammonia and hydrogen having an excess of ammonia and hydrogen reactants in said mixture at contact time in the range from 0.1 to 10 seconds at reaction temperature in the range from about 180° to about 340° C. with a solid catalyst consisting essentially of at least one metal oxide selected from the group consisting of oxides of antimony, tin and manganese on a solid support of alumina at pressure of about one to ten atmospheres, wherein at least 40% of the alkanol converted is selectively converted to monoalkylamine.

2. A process defined by claim 1 wherein the selected catalyst consists essentially of from about 5% to about 30% by weight of selected metal element of the catalytic metal oxide and the remainder of alumina.

3. A process defined by claim 1 wherein the mole ratio of ammonia to alkanol in the gas-phase reaction mixture is in the range from 5 to 1 to about 20 to 1.

4. A process defined by claim 3 wherein the mole ratio of ammonia to hydrogen in the reaction mixture is in the range from about 4 to 1 to about 1 to 4.

* * * * *